United States Patent
Jung et al.

(10) Patent No.: US 10,249,042 B2
(45) Date of Patent: Apr. 2, 2019

(54) METHOD AND APPARATUS FOR PROVIDING MEDICAL INFORMATION SERVICE ON BASIS OF DISEASE MODEL

(71) Applicant: Vuno, Inc., Seoul (KR)

(72) Inventors: Kyuhwan Jung, Seoul (KR); Hyun-Jun Kim, Gyeonggi-do (KR); Sangki Kim, Seoul (KR); Yeha Lee, Gyeonggi-do (KR)

(73) Assignee: Vuno, Inc., Seoul (KR)

( * ) Notice: Subject to any disclaimer, the term of this patent is extended or adjusted under 35 U.S.C. 154(b) by 0 days.

(21) Appl. No.: 15/760,829

(22) PCT Filed: Sep. 24, 2015

(86) PCT No.: PCT/KR2015/010090
§ 371 (c)(1),
(2) Date: Mar. 16, 2018

(87) PCT Pub. No.: WO2017/051945
PCT Pub. Date: Mar. 30, 2017

(65) Prior Publication Data
US 2018/0260954 A1 Sep. 13, 2018

(51) Int. Cl.
*G06T 7/00* (2017.01)
*G06Q 50/22* (2018.01)
*G16H 50/20* (2018.01)
*G16H 30/40* (2018.01)
*G16H 40/63* (2018.01)

(52) U.S. Cl.
CPC .......... *G06T 7/0014* (2013.01); *G06Q 50/22* (2013.01); *G16H 30/40* (2018.01); *G16H 40/63* (2018.01); *G16H 50/20* (2018.01)

(58) Field of Classification Search
USPC .......................................................... 382/128
See application file for complete search history.

(56) References Cited

U.S. PATENT DOCUMENTS

2003/0174872 A1* 9/2003 Chalana ................... G06K 9/00
382/128

FOREIGN PATENT DOCUMENTS

| JP | 2013-191021 A | 9/2013 |
|---|---|---|
| KR | 10-2008-0021181 A | 3/2008 |
| KR | 10-2010-0001730 A | 1/2010 |
| KR | 10-2014-0082385 A | 7/2014 |
| KR | 10-2015-0021327 A | 3/2015 |
| KR | 10-2015-0106491 A | 9/2015 |

OTHER PUBLICATIONS

Hansang Lee et al., "Deep Learning in Medical Imagery", Journal of the Korean Society of Imaging Informatics in Medicine: vol. 20, pp. 13-18, 2014.

* cited by examiner

*Primary Examiner* — Amandeep Saini
(74) *Attorney, Agent, or Firm* — Husch Blackwell LLP

(57) ABSTRACT

According to an embodiment, a method of providing a medical information service is provided. The method for providing a medical information service comprises the steps of: receiving a target image; extracting feature data of the target image; discovering a relative position of the feature data in a disease classification map in which a pre-trained reference image has been quantified; and providing a user with the disease classification map in which the relative position of the feature data has been discovered.

17 Claims, 8 Drawing Sheets

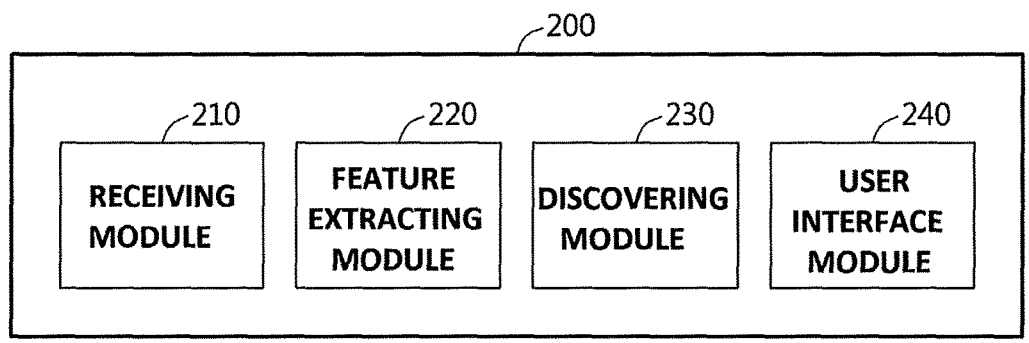
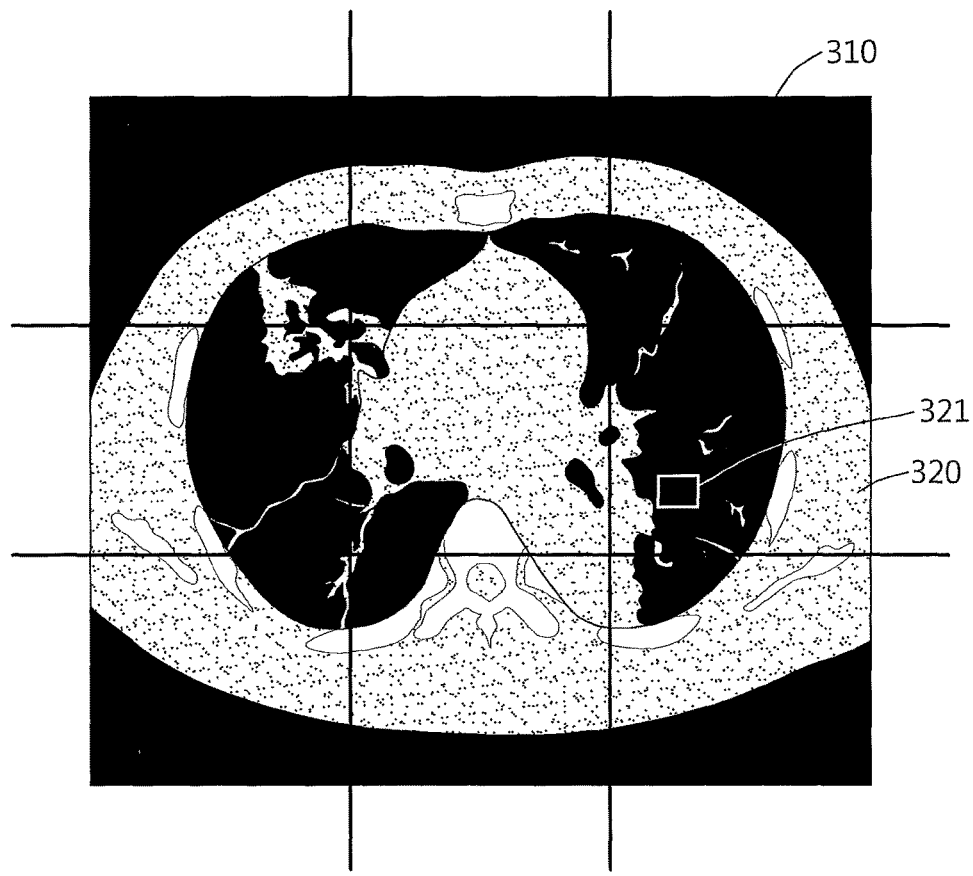

METHOD AND APPARATUS FOR PROVIDING MEDICAL INFORMATION SERVICE ON BASIS OF DISEASE MODEL

CROSS REFERENCE TO RELATED APPLICATIONS

This application is a U.S. National Phase Application of International Application No. PCT/KR2015/010090 filed on Sep. 24, 2015. The disclosure of International Application No. PCT/KR2015/010090 is incorporated herein by reference.

TECHNICAL FIELD

The present disclosure, in its embodiments, relates to a method and apparatus for providing medical information services by quantifying a target image using a model which is trained utilizing a medical image and a diagnosis by a medical personnel.

BACKGROUND ART

Medical imaging apparatuses, including computer tomography (CT), magnetic resonance imaging (MRI), etc., is essential in modern medical science, and the proportion of the role of clinical diagnosis using medical image instruments in medical activities which deal with patients' lives is expected to increase, due to advancements in medical technology.

For convenience of clinical diagnosis, a medical image storage and transmission system (PACS; Picture Archiving and Communication System) is introduced which enables, when necessary, to retrieve a medical image of a subject of interest via a computer monitor in each examination room, after the system converts a medical image (e.g. an X-ray image, CT image, MRI image or ultrasound image) to digital data in a large storage medium which is connected to a server.

INVENTION

Technical Problem

In the conventional medical diagnosis and prescription process, medical personnel analyze the medical image of a subject based on experiences and medical knowledges, and diagnoses it by searching documented information of existing electronic medical records or medical research papers if the reference is required.

However, there are many cases in each of which it takes too much time to search the research papers, which conforms to characteristics shown in the medical image of the subject, or the quality of the search result is bad. Further, in the case of the existing electronic medical records, a subjective finding of the medical personnel is reflected therein, and the medical image itself is not quantified objectively so that its similarity comparison is not so easy.

Therefore, a need is rising for a technology for quantifying the medical image and a technology for retrieving a medical record of a similar subject.

It is an object of the present disclosure to quantify the features of a medical image itself, provide an electronic medical record of the subject who is the most like a target subject, and thereby collect information required for subjective diagnoses and prescriptions.

One objective of the present disclosure is to improve satisfaction with respect to medical service by enhancing the reliability and the understanding toward the diagnosis and prescription for the subject.

Technical Solution

According to an embodiment of the present disclosure, a method for providing medical information service may comprise: receiving a target image; extracting feature data from the target image; discovering a relative position of the feature data in a disease classification map in which a pre-trained reference image is quantified; and providing a user with the disease classification map in which the relative position of the feature data has been discovered.

According to an aspect of the embodiment, the step of extracting the feature data of the target image may include: dividing the target image into a plurality of regions with reference to body structure; extracting a plurality of patches from the plurality of regions; and extracting the feature data from the plurality of patches.

Here, the step of extracting the feature data of the target image may include: obtaining an average value of feature data, which are extracted from the plurality of patches, as each region-wise feature data.

According to another aspect of the embodiment, the step of extracting the feature data may include: extracting an output value of a fully-connected layer which before an output layer in a pre-trained reference image model as the feature data.

According to another aspect of the embodiment, the method for providing medical information service may further comprise: discovering a similar model corresponding to the feature data amongst pre-trained models; and providing the user with the discovered similar model.

Here, the step of discovering the similar model may include: determining whether each of the pre-trained models is similar or not, based on distance value, in a Euclidean space, with respect to the feature data extracted from the each of pre-trained models.

The step of discovering the relative position of the feature data in the disease classification map may include: receiving a past image of a subject corresponding to the target image; extracting past feature data of the received past image; and discovering the relative position of the past feature data in the disease classification map.

The step of discovering the relative position of the feature data in the disease classification map may include: discovering an estimated course of pathway of a target subject using an average from courses of disease pathway of other subjects belonging to a same disease domain in the disease classification map.

The step of discovering the relative position of the feature data in the disease classification map may include: discovering an estimated course of pathway per treatment method for a target subject in the disease classification map.

A method of medical information machine-learning according to an embodiment of the present disclosure may comprise: acquiring a reference image; extracting a patch of the reference image; extracting feature data from the extracted patch; quantifying the reference image based on the feature data and a diagnosis of a medical personnel; creating machine-learning algorithms that quantify the reference image.

According to an aspect of the embodiment, the method of medical information machine-learning may further comprise visualizing a disease classification map by using the quantified reference image.

The disease classification map may divide similar disease patterns, based on each of the disease patterns in a feature space, into a same disease domain.

A medical information service providing apparatus according to an embodiment of the present disclosure may comprise a receiving module receiving a target image; a feature extracting module extracting feature data of the target image; a discovering module discovering a relative position of the feature data in a disease classification map in which a pre-trained reference image is quantified; and a user interface module providing a user with the disease classification map in which the relative position of the feature data has been discovered.

According to an aspect of the embodiment, the discovering module may discover a similar model corresponding to the feature data amongst pre-trained models and the user interface module may provide the user with the discovered similar model.

Here, the discovering module may determine whether each of the pre-trained models is similar or not, based on the distance value, in a Euclidean space, with respect to the feature data extracted from each of the pre-trained models.

According to one aspect of the embodiment, the receiving module may receive a past image of a subject corresponding to the target image, the feature extracting module may extract past feature data of the past image, and the discovering module may discover a relative position of the past feature data in the disease classification map.

According to another aspect of the embodiment, the discovering module may discover an estimated course of pathway of a target subject using an average from courses of disease pathway of other subjects belonging to a same disease domain in the disease classification map.

According to still another aspect of the embodiment, the discovering module may discover an estimated course of pathway per treatment method for a target subject in the disease classification map.

A medical information learning apparatus according to an embodiment of the present disclosure may comprise an acquiring module acquiring a reference image; a patch extracting module extracting a patch of the reference image; a feature extracting module extracting feature data from the extracted patch; a quantifying module quantifying the reference image based on the feature data and a diagnosis of a medical personnel; and a learning module that incorporates machine-learning algorithms to quantify the reference image.

According to an embodiment, the medical information learning apparatus may further comprise a visualizing module, visualizing a disease classification map by using the quantified reference image.

Advantageous Effects

According to the embodiments of the present disclosure, it is possible to diagnose a medical image with higher reliability and consistency and lowering the time of diagnoses by quantifying the features of medical images.

According to the embodiments of the present disclosure, it helps a subject easily understand the conditions thereof by visualizing a condition map and providing it, and it is possible to encourage the subject to actively participate the treatment through understanding of future progression direction.

According to the embodiments of the present disclosure, the accuracy with respect to analysis and diagnosis of a medical image may be enhanced and the reduction of general medical costs and enhancement of medical level may be achieved.

DESCRIPTION OF DRAWINGS

FIG. 2 is a block diagram illustrating a medical information service providing apparatus according to an embodiment of the present disclosure.

FIG. 3 is a diagram illustrating a region and a patch of a medical image according to an embodiment of the present disclosure.

BEST MODE

Hereinafter, embodiments of the present disclosure will be described in detail with reference to the accompanying drawings.

Figure 1:
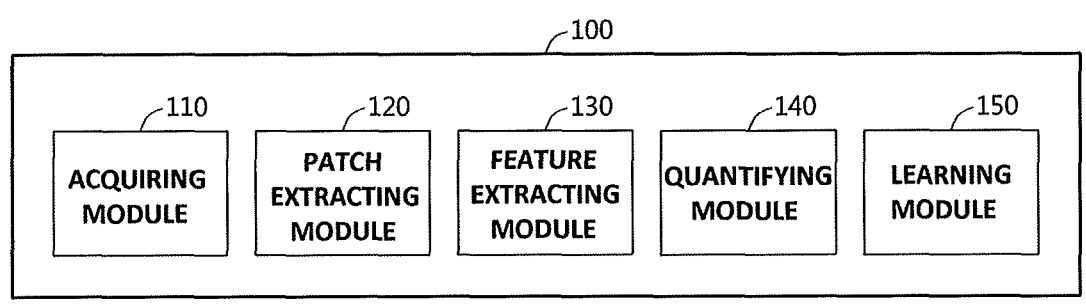
FIG. 1 is a block diagram illustrating a medical information learning apparatus according to an embodiment of the present disclosure.

FIG. 1 is a block diagram illustrating a medical information learning apparatus according to an embodiment of the present disclosure.

Referring to FIG. 1, the medical information learning apparatus 100 according to the embodiment may include an acquiring module 110, a patch extracting module 120, a feature extracting module 130, a quantifying module 140 and a learning module 150. Here, the medical information learning apparatus 100 may calculate the similarity between medical images using features, which uses a deep learning, with respect to a disease of a specific portion based on the medical image.

According to an embodiment, the acquiring module 110 may acquire a reference image. Here, the reference image may include a medical image taken in another clinic. For example, the medical information learning apparatus 100 may acquire the reference image through a server cooperating with a medical imaging system (PACS) or an electronic medical record (EMR). Here, the reference image may include a diagnosis by some medical personnel.

According to an embodiment, the patch extracting module 120 may extract a patch of the reference image. Here, the patch extracting module 120 may divide the reference image into a plurality of regions.

For example, the reference image may be divided into an anterior region (front), a center region and a posterior region (back) with reference to the body structure of a subject. Further, such divided regions may be divided into an inner region, a middle region and an outer region with reference to the center of the body. For another example, the reference image may be divided to an upper region, a center region and a lower region with reference to the body structure of the subject, and the regions may be further divided into a left region, a middle region and a right region.

According to an embodiment, the patch extracting module 120 may extract patches in each region of the divided reference image.

According to an embodiment, the feature extracting module 130 may extract feature data from the extracted patch. Here, the feature data may include an output value of the fully-connected layer which is immediately before the output layer of the medical image patch in the deep learning.

According to an embodiment, the quantifying module 140 may quantify the reference image based on the feature data and a diagnosis by medical personnel. Here, the quantifying module 140 may quantify the medical image into a vector having a dimension as much as the number of the fully-connected layers per region of the medical image.

According to an embodiment, the learning module 150 may learn the quantified reference image. Here, the learning module 150 may train a model with training data as a diagnosis result of the medical personnel and the patch extracted from the reference image using a convolutional neural network. The convolutional neural network may effectively calculate a classification function at a plurality of positions by reusing the partial results in a position in the calculation of an adjacent position. In such a case, the medical image is typically black and white image of 12 bits, and thus, a local response normalization layer may increase the performance.

According to an embodiment, the medical information learning apparatus 100 may further include a visualizing module (not shown). The visualizing module according to an embodiment may visualize a disease classification map using the quantified reference image.

According to an embodiment, the disease classification map may be an image dividing similar disease patterns, based on the disease patterns in a feature space, into the same disease domain. Regarding the disease classification map, it will be specifically described as FIG. 6.

FIG. 2 is a block diagram illustrating a medical information service providing apparatus according to an embodiment of the present disclosure.

Referring to FIG. 2, a medical information service providing apparatus 200 according to the embodiment may comprise a receiving module 210, a feature extracting module 220, a discovering module 230 and a user interface module 240.

According to an embodiment, the receiving 210 may receive a target image. Here, the target image may include a medical image of a target subject.

According to another embodiment, the receiving module 210 may receive a past image of the target subject.

According to an embodiment, the feature extracting module 220 may extract feature data of the target image.

According to an aspect of the embodiment, the feature extracting module 220 may divide the target image into a plurality of regions with reference to body structure, extract patches from the plurality of regions, and extract the feature data from the patches. Here, regarding to the feature data, an average value of feature data, which are extracted from the patches may be from each domain-wise feature data.

According to one aspect, the feature extracting module 220 may extract an output value of a fully-connected layer which is before an output layer in a pre-trained reference image model as the feature data. According to another embodiment, the feature extracting module 220 may extract the feature data of the past image of the target subject.

According to an embodiment, a neural network with deep structure may be pre-trained by a large amount of data. Here, the reference image model may be parameters of each neural network in which numerical values with respect to a connection strength between a node and another node. The feature extracting module 220 may extract, by inputting image data of the target subject, a value of each of the layers up to just before the last output layer as the feature data.

According to an embodiment, the discovering module 230 may discover a relative position of the feature data in the disease classification map. Herein, the disease classification map means a map in which reference images are quantified by the medical image learning apparatus.

According to another embodiment, the discovering module 230 may discover a similar model corresponding to the feature data amongst pre-trained models. For example, the medical information service providing apparatus may discover, using reference images in the medical information learning apparatus, the model which is the most like the target image of the target subject amongst pre-trained models.

According to an aspect of the embodiment, the discovering module 230 may discover the similar model depending on each property information which includes the position, the distribution, and the size of the feature data.

According to another aspect of the embodiment, the discovering module 230 may discover the similar model including all property information.

According to an embodiment, the medical information service providing apparatus may discover a similar subject, based on the quantified value of a medical image, to provide it.

According to one aspect of the embodiment, the discovering module 230 may determine whether each of pre-trained models is similar or not, based on distance value, in a Euclidean space, with respect to the feature data extracted from the pre-trained models.

According to another aspect of the embodiment, the discovering module 230 may obtain a histogram of classification results of the output layer of a trained model with respect to each of the regions which are divided from the medical image. Here, each of the similarities of the feature data and histogram may be obtained and thereafter combined to determine whether it is similar or not.

According to another embodiment, the discovering module 230 may discover a relative position of a past feature data in the disease classification map.

For example, the medical information service providing apparatus may visualize in the disease classification map the feature data of each period-wise medical image of the target subject to visualize a course of disease progression. More specifically, the medical information service providing apparatus may discover the relative position of the past feature data and the relative position of the current feature data of the target subject to visualize them on the disease classification map for providing the user with the visualization.

Here, the user may identify progression of the form change of the disease by adjusting the time axis in the disease classification map.

According to still another embodiment, the discovering module 230 may discover an estimated course of pathway of a target subject using an average from courses of disease pathway of other subjects belonging to a same disease domain in the disease classification map. More specifically, in the case that a first subject currently belongs to a first disease domain, while that other subjects, belonging to the first disease domain, move to a second disease domain 3 months later, it may be predicted that the first subject can belong to the second disease domain the 3 months later according to the average moving pathway of the other subjects.

According to yet another embodiment, the discovering module 230 may discover an estimated course of pathway per treatment method for the target subject in the disease classification map. More specifically, in the case that a first subject currently belongs to a first disease domain, while that other subjects, belonging to the first disease domain, move to a second disease domain 3 months later, it may be predicted that the first subject can belong to the second disease domain the 3 months later according to the average moving pathway of the other subjects.

According to an embodiment, the user interface module 240 may provide the user with a disease classification map in which the relative position of the feature data is discovered. Here, the user interface module 240 may comprise a display apparatus.

FIG. 3 is a diagram illustrating a region and a patch of a medical image according to an embodiment of the present disclosure.

Referring to FIG. 3, a medical image 310 may be divided into a plurality of regions. For example, the medical image 310 may be, as in FIG. 3, divided into a left region, a middle region and a right region, which may be re-divided into an anterior region, a center region, and a posterior region resulting in 9 regions. For another example, the medical image may be divided into an upper region, a center region and a lower region, which may be re-divided into an anterior region, a center region and a posterior region. The medical image may also be divided into an anterior region, a center region, and a posterior region, which may be re-divided into an inner region, a middle region and an outer region. While the regions of the medical image are divided into 9 regions in the embodiment, the number of the regions is not restricted thereto. While an example of a CT image of a lung is shown as a medical image, the medical image may include another portion of a body in another modality.

According to an embodiment, a region 320 may include a patch 321. Herein, the patch 321 means a piece of the medical image.

Figure 4:
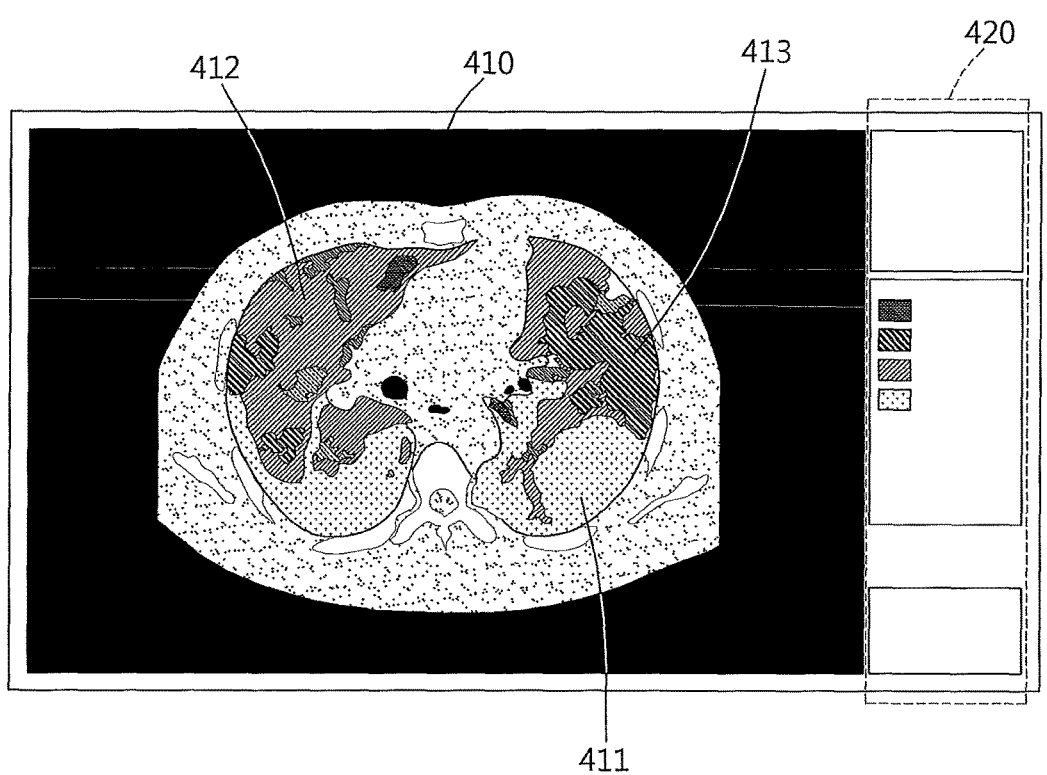
FIG. 4 is a diagram illustrating quantification of a medical image according to an embodiment of the present disclosure.

FIG. 4 is a diagram illustrating quantification of a medical image according to an embodiment of the present disclosure.

Referring to FIG. 4, a medical image 410 may be quantified with varying its color, texture, etc.

For example, as shown in FIG. 4, in order that the patches, having a same feature data, have a same shade, they may be quantified by varying their shades 411, 412, 413. Here, the quantification may be described through a user interface 420.

Figure 5:
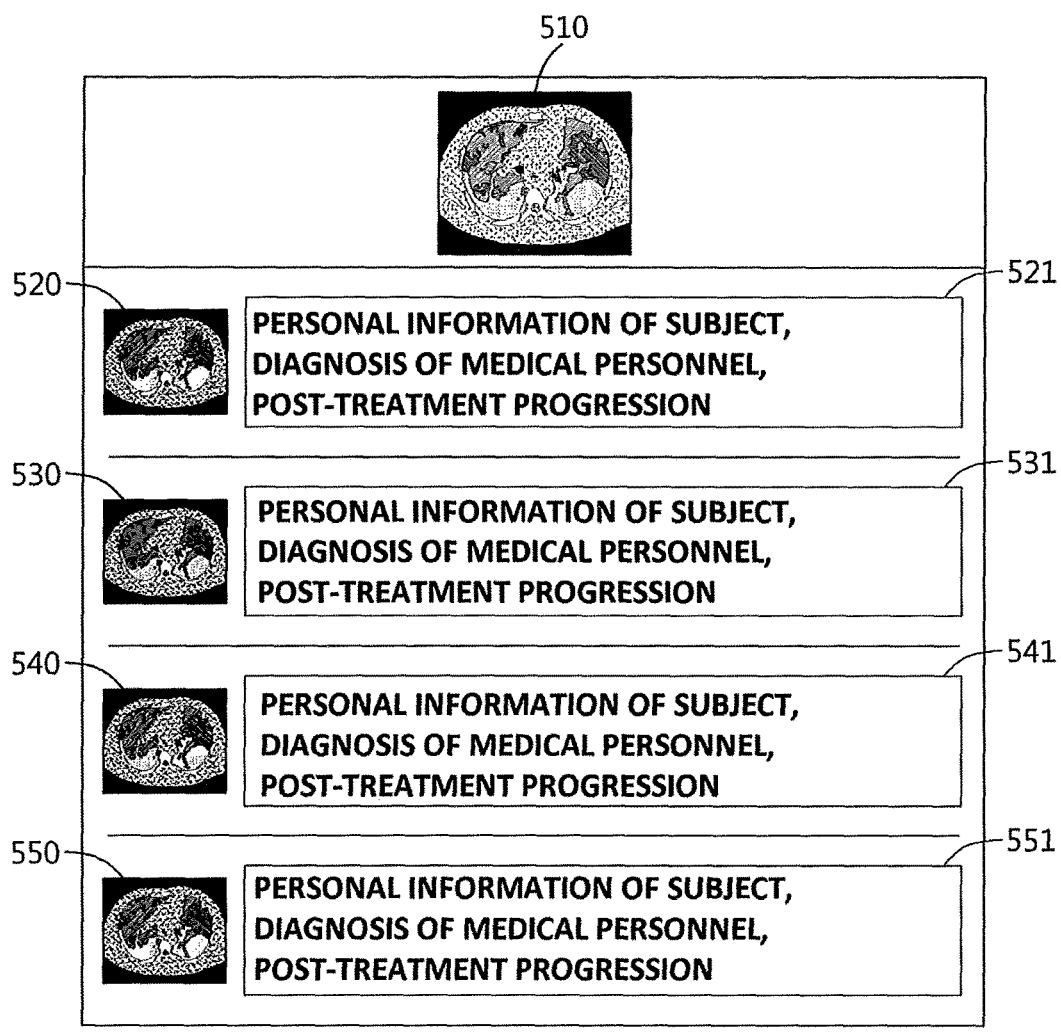
FIG. 5 is a diagram illustrating a user interface for retrieving an electronic medical record of a similar subject according to an embodiment of the present disclosure.

FIG. 5 is a diagram illustrating a user interface for retrieving an electronic medical record of a similar subject according to an embodiment of the present disclosure.

Referring to FIG. 5, the user interface may provide, by retrieving a similar subject having a disease similar to the target image 510 which is a medical image of the target subject, the user with medical images 520, 530, 540, 550 of the similar subject and medial records 521, 531, 541, 551 of the similar subject.

Here, the user interface may provide those amongst the reference images, in the order similar to the target image, with the medical records. That is, a medical image 520 and a medical record 521 of a subject, who is the most similar to the target image 510 of the target subject, may be provided in the first place.

Figure 6:
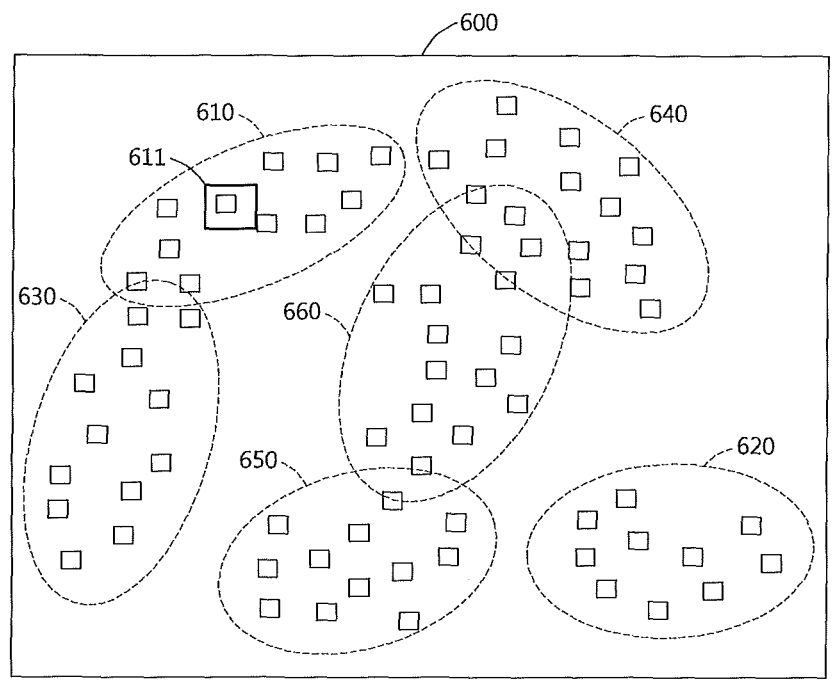
FIG. 6 is a diagram illustrating a disease classification map according to an embodiment of the present disclosure.

FIG. 6 is a diagram illustrating a disease classification map according to an embodiment of the present disclosure.

Referring to FIG. 6, a disease classification map 600 according to the embodiment may be divided into disease domains 610, 620, 630, 640, 650 and 660.

In such a case, the disease classification map may be generated using a dimensionality reduction algorithm which makes two-dimensional or three-dimensional data from the higher dimensional feature data. More specifically, the medical information learning apparatus may learn the feature data from a patch of the reference image through deep learning and may map it into a two-dimensional or three-dimensional space by an unsupervised dimensional reduction algorithm to visualize the result thereof.

According to an embodiment, the medical information learning apparatus may concatenate average positions of feature data in regions, which are divided from the acquired reference images, thereby may use the concatenated result as a feature value of the reference image.

According to an embodiment, the disease classification map 600 may be divided into the predetermined number of disease domains, using feature data of a patch extracted from the medical image. Here, each disease domain may be distinguished based on the property information, such as position, the distribution, the size, etc., of the feature data in the medical image.

For example, in the case that the medical image is a CT image of a lung, a disease domain may be divided depending on division of lung diseases. For example, in a lung CT image, the division of diseases may be normal, lung consolidation, emphysema, GGO (ground-glass opacity), honeycombing and reticular opacity. Therefore, as shown in FIG. 6, the feature data of each of quantified medical images may be divided into disease domains 610, 620, 630, 640, 650, 660 depending on the division of diseases.

The medical information service providing apparatus according to an embodiment may quantify, in the disease classification map 600, at which condition the feature data 611 of the target image of the target subject to visualize it.

While the specific example is described regarding to a lung disease, the present disclosure is not restricted on a lung image or a lung disease, and thus, all the other portions of a body and all the other form of diseases may be learned and quantified.

The disease classification map according to an embodiment may indicate that it is the more dangerous condition in the case of being farther away from the normal domain.

Figure 7:
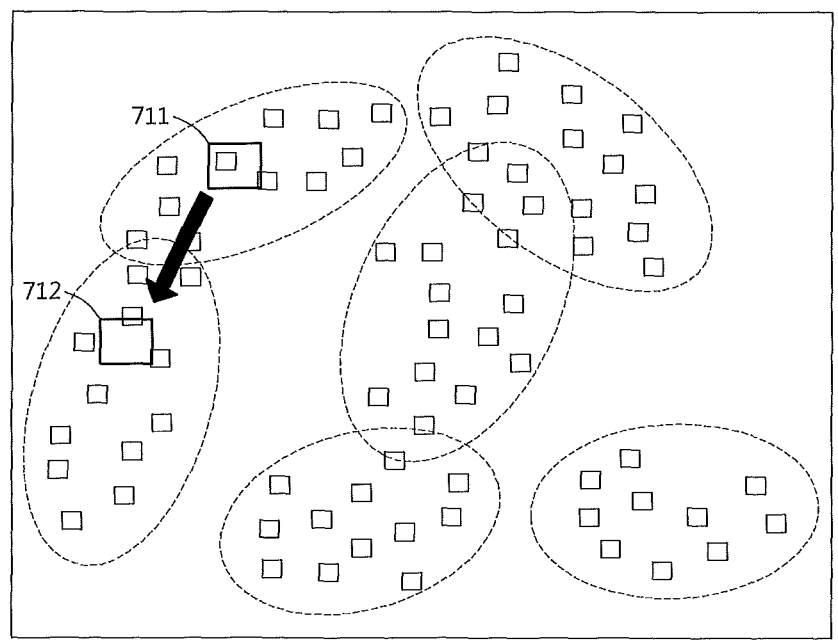
FIG. 7 is a diagram illustrating a disease classification map which visualizes the course of pathway of a target subject.

FIG. 7 is a diagram illustrating a disease classification map which visualizes the course of pathway of a target subject.

Referring to FIG. 7, the medical information service apparatus according to an embodiment may discover, from the current position 711 of a subject in a disease classification map, an estimated position 712 of the same subject 3 months later. Here, the medical information service apparatus may discover an estimated course of the pathway of the target subject using an average from courses of the disease pathway of other subjects belonging to a same disease domain in the disease classification map. More specifically, in the case that a first subject currently belongs to a first disease domain, while that other subjects, belonging to the first disease domain, move to a second disease domain 3 months later, it may be predicted that the first subject can belong to the second disease domain the 3 months later according to the average moving pathway of the other subjects.

As described in connection with FIG. 7, the medical information service apparatus according to the embodiment may awake awareness of a subject by predicting a future course of disease progression and provide the subject with it.

Figure 8:
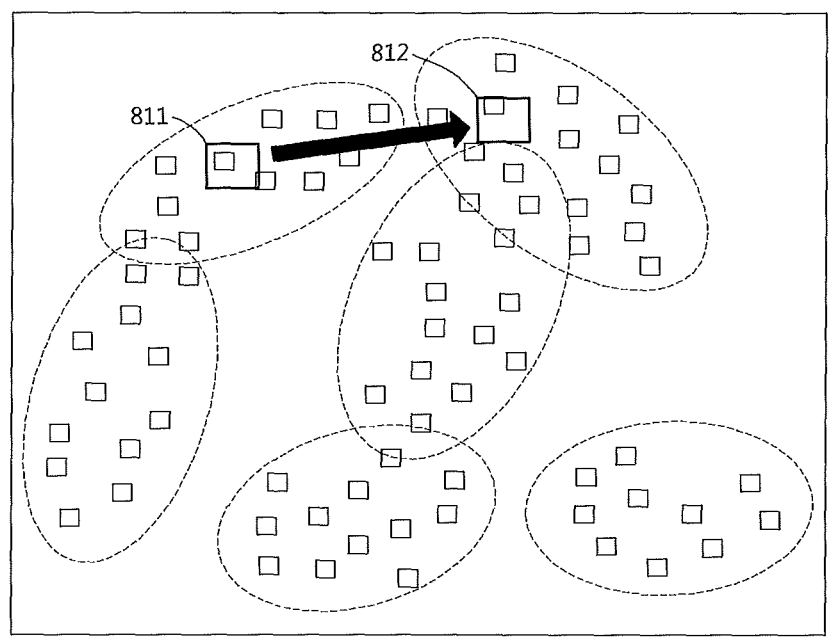
FIG. 8 is a diagram illustrating a disease classification map which visualizes the estimated course which depends on the treatment method.

FIG. 8 is a diagram illustrating a disease classification map which visualizes the estimated course which depends on the treatment method.

Referring to FIG. 8, the medical information service apparatus according to an embodiment may discover, from the current position 811 of a subject in a disease classification map, an estimated position 812 of the same subject after treatment. Here, the medical information service providing apparatus may discover the estimated course of the pathway of the target subject using an average of disease courses of the pathway in the event that other subjects belonging to the same disease domain in the disease classification map receive the same treatment. More specifically, in the case that a first subject currently belongs to a first disease domain, while that other subjects, belonging to the first disease domain, move to a second disease domain 3 months later, it may be predicted that the first subject can belong to the second disease domain the 3 months later according to the average moving pathway of the other subjects.

For another example, the medical information service providing apparatus may allow the user to select a treatment method by referring to a course of the pathway, in the disease classification map, according to the treatment method of another subject.

As described in connection with FIG. 8, the medical information service apparatus according to an embodiment may induce the subjects themselves to actively participate in the treatment process by informing them of the need of the treatment.

Figure 9:
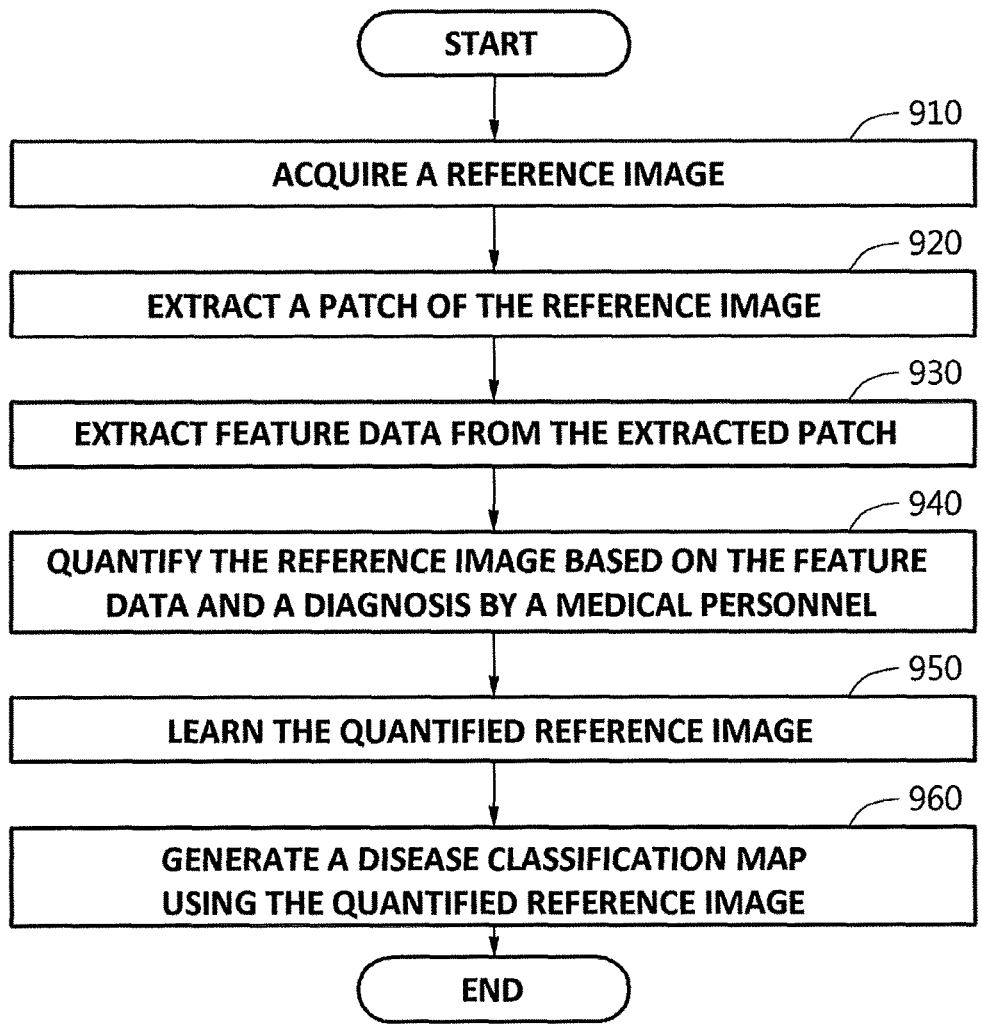
FIG. 9 is a flow chart illustrating a method of medical information machine-learning according to an embodiment of the present disclosure.

FIG. 9 is a flow chart illustrating a method of medical information machine-learning according to an embodiment of the present disclosure.

Referring to FIG. 9, in step of 910, the medical information learning apparatus according to an embodiment may acquire a reference image. In the step, the reference image may include medical images of other subjects. For example, the medical information learning apparatus may acquire the reference image through a server cooperating with a medical imaging system (PACS) or an electronic medical record (EMR). Here, the reference image may include a diagnosis by medical personnel.

In step of 920, the medical information learning apparatus according to the embodiment may extract a patch of the reference image.

In an aspect of the embodiment, the medical information learning apparatus may divide the reference image into a plurality of regions. For example, the reference image may be divided into an anterior region (front), a center region and a posterior region (back) with reference to the body structure of a subject. Further, such divided regions may be divided into an inner region, a middle region and an outer region with reference to the center of the body. For another example, the reference image may be divided to an upper region, a center region and a lower region with reference to the body structure of the subject, and the regions may be further divided into a left region, a middle region and a right region.

According to an embodiment, the patch extracting module 120 may extract patches in each divided region of the reference image.

In step of 930, the medical information learning apparatus according to the embodiment may extract feature data from the extracted patch. Here, the feature data may include an output value of a fully-connected layer which is immediately before an output layer of the medical image patch in deep learning.

In step of 940, the medical information learning apparatus according to the embodiment may quantify the reference image based on the feature data and a diagnosis by medical personnel. The medical information learning apparatus may quantify the medical image to a vector having a dimension as much as the number of the fully-connected layers per region of the medical image.

In step of 950, the medical information learning apparatus according to the embodiment may learn the quantified reference image. The medical information learning apparatus may train a model with training data as a diagnosis result of the medical personnel and the patch extracted from the reference image using a convolutional neural network. The convolutional neural network may effectively calculate a classification function at a plurality of positions by reusing the partial results in a position in the calculation of an adjacent position. In such a case, the medical image is typically black and white image of 12 bits, and thus, a local response normalization layer may increase the performance.

In step of 960, the medical information learning apparatus according to the embodiment may generate a disease classification map using the quantified reference images. According to an embodiment, the disease classification map may be an image dividing similar disease patterns, based on the disease patterns in a feature space, into a same disease domain.

Figure 10:
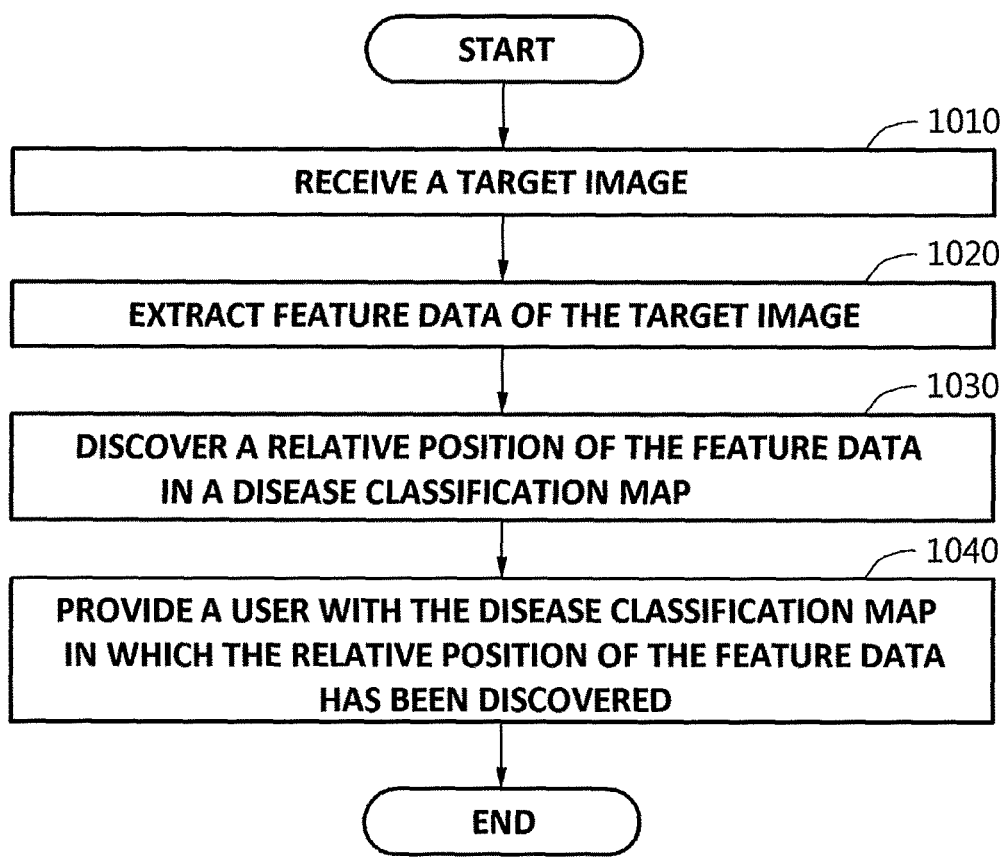
FIG. 10 is a flow chart illustrating a method for providing medical information service according to an embodiment of the present disclosure.

FIG. 10 is a flow chart illustrating a method for providing medical information service according to an embodiment of the present disclosure.

Referring to FIG. 10, in step of 1010, the medical information service providing apparatus according to an embodiment may receive a target image.

In step of 1020, the medical information service providing apparatus according to an embodiment may extract feature data of the target image.

According to an embodiment, the step of 1020 may include dividing the target image into a plurality of regions with reference to body structure, extracting a plurality of patches from the plurality of regions, and extracting the feature data from the plurality of patches.

Here, the step of 1020 may include assigning an average value of feature data, which are extracted from the patches, to each domain-wise feature data.

According to another embodiment, the step of 1020 may include extracting an output value of a fully-connected layer, which is prior to an output layer in a pre-trained reference image model as the feature data.

In step of 1030, the medical information service providing apparatus according to an embodiment may discover the relative position of the feature data in the disease classification map.

According to an embodiment, the step of 1030 may include receiving a past image of a subject corresponding to the target image, extracting past feature data of the received past image, and discovering the relative position of the past feature data in the disease classification map.

According to another embodiment, the step of 1030 may include discovering an estimated course of pathway of a target subject using an average from courses of the disease pathway of other subjects belonging to a same disease domain in the disease classification map.

According to still another embodiment, the step of 1030 may include discovering an estimated course of pathway per treatment method for a target subject in the disease classification map.

In step of 1040, the medical information service providing apparatus according to an embodiment may provide a user with the disease classification map in which the relative position of the feature data has been discovered.

According to an embodiment, the method for providing a medical information service may further comprise discovering a similar model corresponding to the feature data amongst pre-trained models, and providing the user with the discovered similar model.

Here, the step of discovering the similar model may include determining whether each of the pre-trained models is similar or not, based on distance value, in a Euclidean space, with respect to the feature data extracted from the each of pre-trained models.

The method according to the embodiments may be implemented as a form of program instructions capable to be executed through a variety of computer means to be stored in a computer readable medium. The computer readable medium may contain program instructions, data files, data structures, etc., independently or in combination. The program instructions stored in the medium may be specifically designed and configured for the embodiments or available by being known to a person having ordinary skill in the computer software field. Examples of the computer readable record medium may include a magnetic medium, such as a hard disk, a floppy disk and a magnetic tape, an optical medium such as CD-ROM and DVD, a magneto-optical medium such as a floptical disk, and a hardware device specifically configured to store and perform the program instructions such as a ROM, a RAM, a flash memory, etc. Examples of the computer instructions may include machine language code as generated by a compiler as well as high-level language code which may be executed by a computer using an interpreter, etc. The above-mentioned hardware device may be configured to operate as one or more software modules for performing the operations of the embodiments and vice versa.

While certain embodiments have been described with the limited drawings, a person having ordinary skill in the art may variously modify and change them from the aforesaid. For example, a proper result may be achieved even if the described technologies are performed in an order different from the described order, and/or if the described components such as a system, structure, apparatus, circuit, etc. are connected or combined in a form different from the described, and/or if the components are substituted or replaced by another component or an equivalent. Therefore, another implementation, another embodiment and equivalents of the following claims belong to the scope of the following claims.

What is claimed is:
1. A method for providing medical information service, comprising:
(a) receiving, by a medical information service providing apparatus, a target image;
(b) extracting, by the medical information service providing apparatus, feature data of the target image using a convolutional neural network;
(c) discovering, by the medical information service providing apparatus, a relative position of the feature data in a disease classification map which is generated by mapping reference feature data of a reference image quantified in a reference image model, which model is pre-trained by the convolutional neural network, into a two-dimensional or three-dimensional space by a dimensionality reduction algorithm, wherein the disease classification map is divided into a plurality of disease domains, based on the reference feature data of a patch extracted from the reference image, on a feature space, the disease domains are distinguished based on a property information of the reference feature data, the property information includes at least one of a position, a distribution and a size, in the reference image, of the reference feature data; and
(d) providing, by the medical information service providing apparatus, a user with the disease classification map in which the relative position of the feature data has been discovered, and
wherein the disease classification map divides similar disease patterns, based on each of the disease patterns in the feature space, into a same disease domain.
2. The method of claim 1, wherein (b) extracting the feature data of the target image includes:
(b1) dividing, by the medical information service providing apparatus, the target image into a plurality of regions with reference to body structure;
(b2) extracting, by the medical information service providing apparatus, a plurality of patches from the plurality of regions; and
(b3) extracting, by the medical information service providing apparatus, the feature data from the plurality of patches.
3. The method of claim 2, wherein (b) extracting the feature data of the target image includes:
(b4) obtaining, by the medical information service providing apparatus, an average value of feature data, which are extracted from the plurality of patches, as each region-wise feature data.
4. The method of claim 1, wherein (b) extracting the feature data includes:
extracting, by the medical information service providing apparatus, an output value of a fully-connected layer which is prior to an output layer in a pre-trained reference image model as the feature data.
5. The method of claim 1, further comprising:
(e) discovering, by the medical information service providing apparatus, a similar model corresponding to the feature data amongst pre-trained models; and
(f) providing, by the medical information service providing apparatus, the user with the discovered similar model.
6. The method of claim 5, wherein (e) discovering the similar model includes:
determining, by the medical information service providing apparatus, whether each of the pre-trained models is similar or not, based on distance value, in a Euclidean space, with respect to the feature data extracted from the each of pre-trained models.
7. The method of claim 1, wherein (c) discovering the relative position of the feature data in the disease classification map includes:

(c1) receiving, by the medical information service providing apparatus, a past image of a subject corresponding to the target image;
(c2) extracting, by the medical information service providing apparatus, past feature data of the received past image; and
(c3) discovering, by the medical information service providing apparatus, the relative position of the past feature data in the disease classification map.

8. The method of claim 1, wherein (c) discovering the relative position of the feature data in the disease classification map includes:
discovering, by the medical information service providing apparatus, an estimated course of pathway of a target subject using an average from courses of disease pathway of other subjects belonging to a same disease domain in the disease classification map.

9. The method of claim 1, wherein (c) discovering the relative position of the feature data in the disease classification map includes:
discovering, by the medical information service providing apparatus, an estimated course of pathway per treatment method for a target subject in the disease classification map.

10. A method of medical information machine-learning, comprising:
(a) acquiring, by a medical information learning apparatus, a reference image;
(b) extracting, by the medical information learning apparatus, a patch of the acquired reference image;
(c) extracting, by the medical information learning apparatus, feature data from the extracted patch using a convolutional neural network;
(d) quantifying, by the medical information learning apparatus, the reference image based on the feature data and a diagnosis of a medical personnel;
(e) machine-learning, by the medical information learning apparatus, the quantified reference image using the convolutional neural network to generate a reference image model; and
(f) visualizing, by the medical information learning apparatus, a disease classification map by mapping reference feature data corresponding to the quantified reference image into a two-dimensional or three-dimensional space by a dimensionality reduction algorithm, wherein the disease classification map is divided into a plurality of disease domains, based on the reference feature data of a patch extracted from the reference image, on a feature space, the disease domains are distinguished based on a property information of the reference feature data, the property information includes at least one of a position, a distribution and a size, in the reference image, of the reference feature data, and
wherein the disease classification map divides similar disease patterns, based on each of the disease patterns in the feature space, into a same disease domain.

11. A medical information service providing apparatus, comprising:
a receiving module receiving a target image;
a feature extracting module extracting feature data of the target image using a convolutional neural network;
a discovering module discovering a relative position of the feature data in a disease classification map which is generated by mapping reference feature data of a reference image quantified in a reference image model, which model is pre-trained by the convolutional neural network, into a two-dimensional or three-dimensional space by a dimensionality reduction algorithm, wherein the disease classification map is divided into a plurality of disease domains, based on the reference feature data of a patch extracted from the reference image, on a feature space, the disease domains are distinguished based on a property information of the reference feature data, the property information includes at least one of a position, a distribution and a size, in the reference image, of the reference feature data; and
a user interface module providing a user with the disease classification map in which the relative position of the feature data has been discovered, and
wherein the disease classification map divides similar disease patterns, based on each of the disease patterns in the feature space, into a same disease domain.

12. The apparatus of claim 11, wherein the discovering module discovers a similar model corresponding to the feature data amongst pre-trained models and the user interface module provides the user with the discovered similar model.

13. The apparatus of claim 12, wherein the discovering module determines whether each of the pre-trained models is similar or not, based on distance value, in a Euclidean space, with respect to the feature data extracted from the each of pre-trained models.

14. The apparatus of claim 11, wherein the receiving module receives a past image of a subject corresponding to the target image,
the feature extracting module extracts past feature data of the past image, and
the discovering module discovers a relative position of the past feature data in the disease classification map.

15. The apparatus of claim 11, wherein the discovering module discovers an estimated course of pathway of a target subject using an average from courses of disease pathway of other subjects belonging to a same disease domain in the disease classification map.

16. The apparatus of claim 11, wherein the discovering module discovers an estimated course of pathway per treatment method for a target subject in the disease classification map.

17. A medical information learning apparatus, comprising:
an acquiring module acquiring a reference image;
a patch extracting module extracting a patch of the reference image;
a feature extracting module extracting feature data from the extracted patch using a convolutional neural network;
a quantifying module quantifying the reference image based on the feature data and a diagnosis of a medical personnel;
a learning module machine-learning the quantified reference image using the convolutional neural network to generate a reference image model; and
a visualizing module visualizing, by the medical information learning apparatus, a disease classification map by mapping reference feature data corresponding to the quantified reference image into a two-dimensional or three-dimensional space by a dimensionality reduction algorithm, wherein the disease classification map is divided into a plurality of disease domains, based on the reference feature data of a patch extracted from the reference image, on a feature space, the disease domains are distinguished based on a property information of the reference feature data, the property information includes at least one of a position, a distribution and a size, in the reference image, of the reference feature data, and wherein the disease classification map divides similar disease patterns, based on each of the disease patterns in the feature space, into a same disease domain.

\* \* \* \* \*